United States Patent [19]

Chin

[11] Patent Number: 4,878,893
[45] Date of Patent: Nov. 7, 1989

[54] ANGIOSCOPE WITH FLUSH SOLUTION DEFLECTOR SHIELD

[75] Inventor: Albert K. Chin, Palo Alto, Calif.

[73] Assignee: Thomas J. Fogarty, Palo Alto, Calif.

[21] Appl. No.: 187,482

[22] Filed: Apr. 28, 1988

[51] Int. Cl.<sup>4</sup> ............................................... A61B 1/12
[52] U.S. Cl. ..................................... 604/21; 604/105; 128/4; 128/345
[58] Field of Search ............................ 604/104–107, 604/20–21, 52, 56, 82–83, 93, 181–187; 128/4, 341, 345

[56] References Cited

U.S. PATENT DOCUMENTS

| | | | |
|---|---|---|---|
| 3,938,530 | 2/1976 | Santomieri | 604/105 |
| 4,175,545 | 11/1979 | Termanini | 604/21 X |
| 4,250,873 | 2/1981 | Bonnet | 128/341 X |
| 4,608,965 | 9/1986 | Anspach et al. | 604/105 X |
| 4,781,682 | 11/1988 | Patel | 604/104 X |

Primary Examiner—Angela D. Sykes
Attorney, Agent, or Firm—Limbach, Limbach & Sutton

[57] ABSTRACT

The present invention provides an angioscope catheter for visualizing the interior of a vessel, such as an artery. The angioscope catheter includes an angioscope having a distal viewing end, an irrigating catheter that includes structure for introducing flush solution to the interior of the vessel at the distal end of the angioscope, and a deflector shield mounted at the distal end of the angioscope such that flush solution introduced by the catheter impacts on the deflector shield.

3 Claims, 2 Drawing Sheets

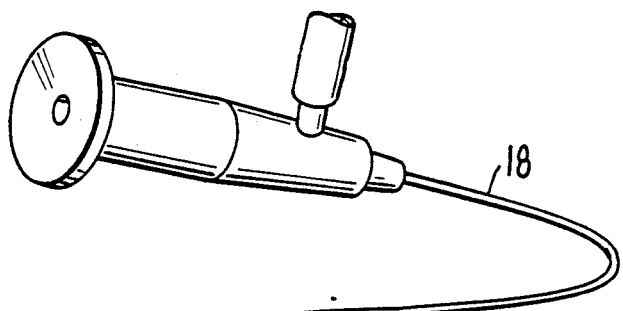
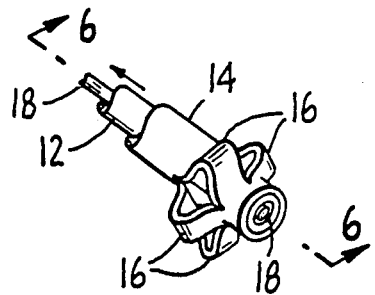
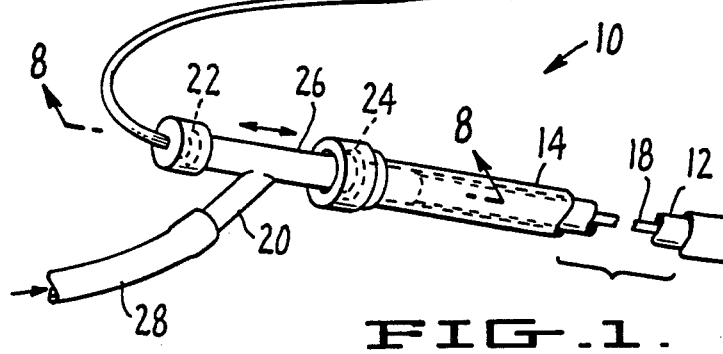
FIG.1.  FIG.2.
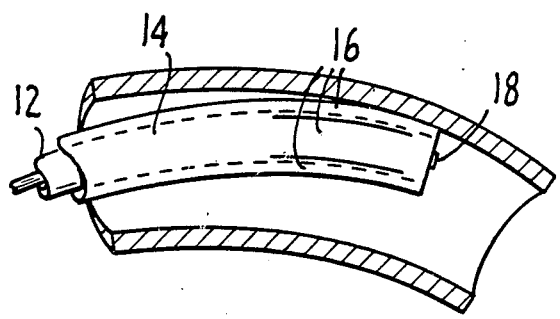
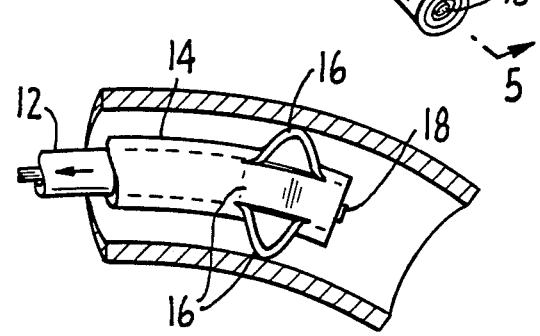
FIG.3.  FIG.4.
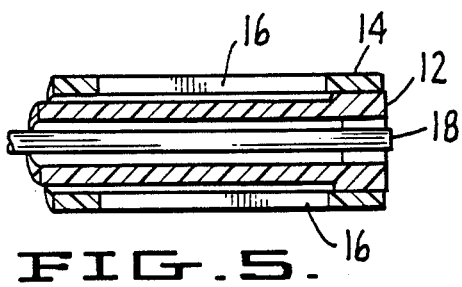
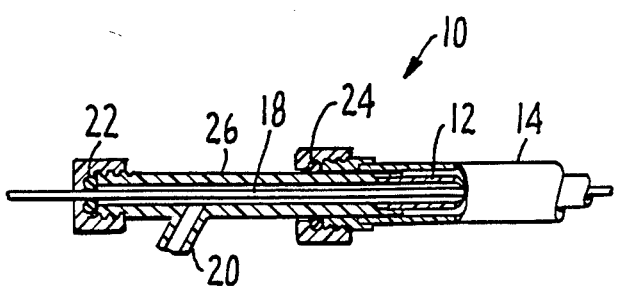
FIG.5.  FIG.8.
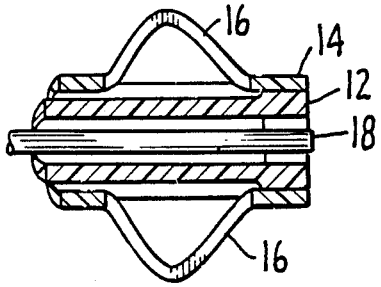
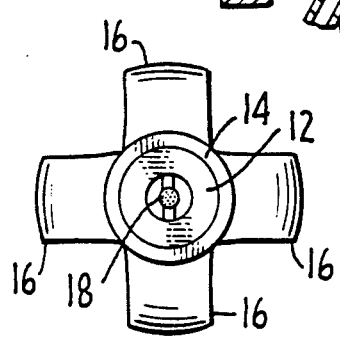
FIG.6.  FIG.7.

ANGIOSCOPE WITH FLUSH SOLUTION DEFLECTOR SHIELD

BACKGROUND OF THE INVENTION

1. Field of the Invention

The present invention relates to apparatus for direct visualization of body passages and, in particular, to a catheter structure which allows an angioscope to be centered within a blood vessel during visualization while maintaining blood flow.

2. Discussion of the Prior Art

Optical scopes have been in use for some time for direct visualization of body passages. For example, endoscopes are used for viewing the gastrointestinal tract, bronchoscopes are used for viewing bronchial passages and arthroscopes are used for joint examination. These scopes are attached to a video camera which displays the image on a video monitor or, alternatively, the body passage is viewed directly through the eyepiece of the scope.

An angioscope is used for visualization in both the arterial and the venous systems. Typically, the angioscope is inserted into the artery or vein through an incision and then periodically advanced to obtain visualization at desired locations along a length o the vessel.

Angioscopy is a particularly difficult procedure in the arterial system. The pressure and the flow rate of blood are much higher in the arteries than in the veins, making it difficult to obtain the bloodless field required for the desired quality of visualization.

Typically, an angioscope is combined with a catheter which is used to introduce a bolus of sterile saline solution into the vessel at the distal end of the angioscope to provide a clear viewing field. However, particularly in the arterial system, if only a small amount of saline is used, the blood washes the saline flush away too quickly to allow visual examination. On the other hand, if a larger amount of flush solution is used, over a time period sufficient to allow adequate visualization, complications will arise. First, fluid overload of the patient will occur, causing electrolyte imbalance or congestive heart failure. Second, there will be a lack of perfusion to the tissue supplied by the artery undergoing angioscopy because the flush solution has cleared away the oxygen-carrying blood. This problem is particularly difficult in angioscopic evaluation of the coronary arteries, since cardiac muscle cannot tolerate prolonged ischemia. Balloon occlusion may be used, but it too may cause ischemia.

An additional major problem that is encountered in conventional angioscopy is that, during visualization, particularly in curved sections of the vessel, the angioscope lies against the wall of the vessel, obstructing the view. Balloon catheters have been used for centering the angioscope. However, as stated above, inflation of the balloon occludes the vessel. In addition, centering catheters that use balloons require an additional catheter lumen to inflate the balloon. This extra lumen either decreases the size of the irrigating lumen or increases the size of the centering catheter.

SUMMARY OF THE INVENTION

The present invention provides an angioscope catheter for visualizing the interior of a vessel, such as an artery. The angioscope catheter includes an angioscope having a distal viewing end, an irrigating catheter that includes means for introducing flush solution to the interior of the vessel at the distal end of the angioscope, and a deflector shield mounted at the distal end of the angioscope such that flush solution introduced by the catheter impacts on the deflector shield. The angioscope catheter is centered by structure comprising an inner catheter which slides longitudinally relative to an outer sheath. The outer sheath includes a set of longitudinal slitted sections formed circumferentially near its distal tip. The outer sheath and inner catheter are bonded at their distal-most points. Thus, when the inner catheter is pulled proximally with respect to the outer sheath, the slitted sections in the outer sheath splay out radially in a symmetrical fashion about the longitudinal axis of the catheter. This centers the angioscope during visualization in curved sections of the vessel, while allowing blood to flow past the splayed slitted sections.

The deflector is provided at the tip of the catheter so that a bolus of saline solution can be introduced with blood flow to successfully provide a clear viewing field for the angioscope.

A better understanding of the features and advantages of the present invention will be obtained by reference to the following detailed description of the invention and accompanying drawings which set forth an illustrative embodiment in which the principles of the invention are utilized.

DESCRIPTION OF THE DRAWINGS

FIG. 1 is a pictorial view illustrating an angioscope centering catheter in accordance with the present invention.

FIG. 2 is a detailed pictorial view illustrating the distal end of the angioscope centering catheter shown in FIG. 1 with slitted sections splayed out to center the catheter in accordance with the present invention.

FIG. 3 is a cross-sectional view of a curved portion of a vessel illustrating an angioscope centering catheter prior to splaying of the slitted sections.

FIG. 4 is a cross-sectional view of a curved section of a vessel illustrating an angioscope centering catheter after splaying of the slitted sections.

FIG. 5 is a cross-sectional view taken along line 5—5 in FIG. 1 illustrating the distal end of an angioscope centering catheter prior to splaying of the slitted sections.

FIG. 6 is a cross-sectional view taken along line 6—6 in FIG. 2 illustrating the distal end of an angioscope centering catheter after splaying of the slitted sections.

FIG. 7 is an end view illustrating the distal end of an angioscope centering catheter after splaying of the slitted sections.

FIG. 8 is a cross-sectional view taken along line 8—8 in FIG. 1 illustrating an irrigation port of an angioscope centering catheter.

DETAILED DESCRIPTION OF THE INVENTION

Figure 9:
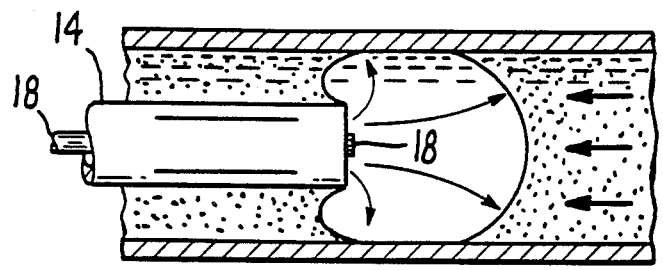
FIG. 9 is a cross-sectional view of a vessel illustrating introduction of a bolus of flushing solution against blood flow.

An angioscope centering catheter 10 in accordance with the present invention is illustrated in FIG. 1.

The angioscope centering catheter 10 comprises an inner catheter 12 which slides longitudinally relative to an outer sheath 14. The catheter 12 and outer sheath 14 may be fabricated of any suitable polymer material capable of bending to conform to the shape of the vessel, such as an artery, through which the assembly is directed.

According to one aspect of the present invention, the outer sheath 14 includes a plurality of longitudinal slitted sections 16 which are circumferentially and symmetrically formed near its distal tip. As best shown in FIGS. 5 and 6, the outer sheath 14 is bonded to the inner catheter 12 at their distal-most points. Thus, when the inner catheter 12 is pulled proximally with the outer sheath 14 held fixed, the slitted sections 16 in the outer sheath 14 splay out radially in a symmetrical fashion about the longitudinal axis of the catheter 10. This splaying action forces the catheter 10 away from the walls of the vessel and centers the angioscope 18 during visualization, particularly in curved sections of the vessel, as shown in FIGS. 3 and 4. At the same time, it allows blood to flow past the splayed slitted sections 16.

The outer sheath 14 may be of various outer diameters ranging from about 5 French (1.67 mm) to 12 French (4.0 mm). The longitudinal slits for an outer sheath 14 of a given diameter may vary in length, longer slits causing slitted sections 16 to splay out to a larger diameter than shorter slits. According to one embodiment, 5-6 mm long slits are used in an 8 French (2.7 mm diameter) outer sheath. This ratio of slit length to sheath diameter is believed to be optimal. If the slits are too short, it will be difficult to pull back on the inner catheter 12 to achieve the splayed configuration.

The angioscope 18 comprises an illuminated fiberoptic scope which extends through the inner catheter 12 for viewing through the open distal end of the catheter, as best illustrated in FIGS. 5-7. The fiberoptic scope may be of the type manufactured by Baxter, Edwards LIS Division, Santa Ana, California. Such scopes have central viewing strands which are surrounded by peripheral illuminating strands. Although not illustrated, it should be understood that the proximal end of the angioscope 18 would be secured to a suitable viewer, such as a magnifying eyepiece or video camera.

A particular application of an angioscope centering catheter in accordance with the present invention is described in co-pending U.S. Pat. Application Ser. No. 187,591, titled REAL TIME ANGIOSCOPY IMAGING SYSTEM, filed by Chin et al of even date herewith, which application is commonly-assigned herewith to Dr. Thomas J. Fogarty and is hereby incorporated by reference to provide additional background for the present invention.

Referring to FIG. 8, the angioscope centering catheter 10 also includes an irrigation port 20 for introducing flushing solution into the vessel through the inner catheter 12.

The angioscope centering catheter is irrigated, typically with sterile saline, via the irrigation port 20 by means of an irrigation line 28 connected to a saline pressure system (not shown). Although it does not constitute an element of the present invention, a typical pressure system could include a pressure vessel that houses a bag of sterile saline which is attached to the irrigation line 28 by means of an irrigation line spike. An 0-ring seals the irrigation line spike against the cover of the pressure vessel. Compressed air is supplied to the pressure vessel via an inlet. The required pressure is adjusted by a regulator at the inlet and the pressure inside the pressure vessel is measured by a pressure gauge. Pulses of pressurized saline may then be delivered on command from a computer, which opens and closes a solenoid pinch valve. The solenoid pinch valve pinches a section of silicone tubing which lies in line with the irrigation line 28. The computer may be programmed to deliver a sequence of timed irrigations or a single pulse may be delivered by means of a foot pedal switch connected to the computer.

This type of automated irrigation system is described in greater detail in the above-identified application by Chin et al.

Referring back to FIG. 8, the angioscope 18 is held in place within the inner catheter 12 by means of an 0-ring seal 22. A second 0-ring seal 24 prevents blood from seeping out between the inner catheter 12 and the outer sheath 14. This second 0-ring seal 24 slides longitudinally along a rigid section 26 housing the inner catheter 12. The rigid section 26 permits easy movement of the outer sheath 14 and the inner catheter 12 with respect to one another, to facilitate splaying of the slitted sections 16 as described above.

Figure 10:
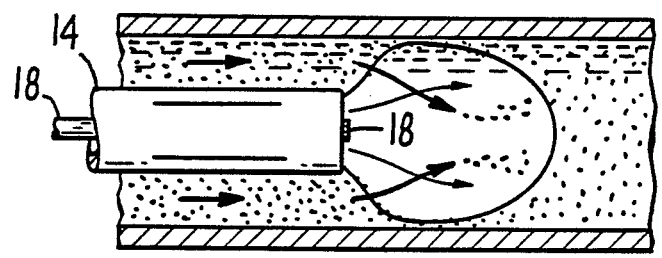
FIG. 10 is a cross-sectional view of a vessel illustrating introduction of a bolus of flushing solution with blood flow.

As stated above, a bolus of flushing solution can be introduced to the vessel via the inner catheter 12 to create a clear viewing field at the tip of the angioscope 18. As shown in FIG. 9, by controlling the volume of flushing solution and the pressure at which it is introduced, a bolus introduced against blood flow will create a clear viewing field for a desired, albeit short, period of time. However, as shown in FIG. 10, if the bolus of flushing solution is introduced with blood flow, then the flow of blood will instantaneously dilute the flush solution, making it difficult to achieve visualization.

The catheter design used to flush against blood flow will vary with the situation and the application. For intraoperative angioscopy, the artery will be isolated in the operating room and an arteriotomy made to admit the angioscope. The artery will be clamped proximal and distal to the arteriotomy site. If the angioscope is advanced in a distal direction, there is no forward blood flow, only back flow from collateral side branches. Thus, the flushing catheter may be a straight, open ended catheter as shown in FIG. 9. If the angioscope is advanced in a proximal direction, it is again going against blood flow. A straight, open end catheter will again be appropriate.

For percutaneous angioscopy, the angioscope is introduced via a needle puncture, through an introducing sheath into the artery. Usually, the access site is the femoral artery. If the angioscope is threaded distally, it lies in the same direction as the blood flow. The conventional catheter will experience the dilution problems described above with respect to FIG. 10.

Figure 11:
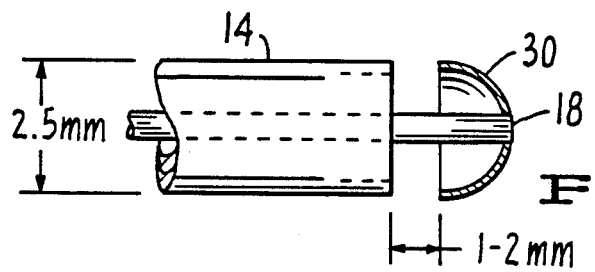
FIG. 11 is a partial cross-sectional view illustrating a deflector shield mounted at the distal end of an angioscope centering catheter in accordance with the present invention.

In accordance with another aspect of the present invention, as shown in FIG. 11, a curved deflector shield 30 is provided at the distal tip of the catheter 10 so that a bolus of flushing solution can be introduced with blood flow to successfully provide a clear viewing field for angioscope 18.

Figure 12:
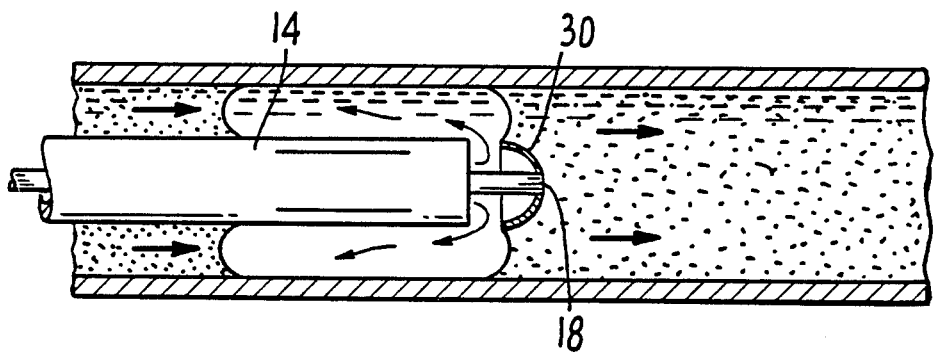
FIG. 12 is a cross-sectional view of a vessel illustrating deflection of a bolus of flushing solution introduced with blood flow.
Figure 13:
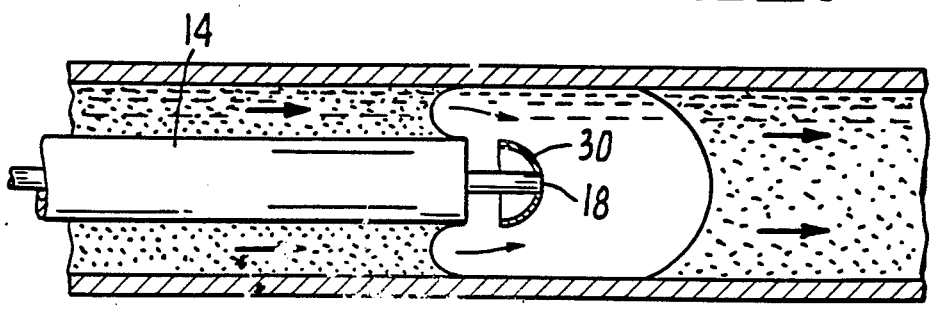
FIG. 13 is a cross-sectional view of a vessel illustrating creation of a visualization field by deflected introduction of a bolus of flushing solution with blood flow.

As shown in FIG. 12, the deflector shield causes the flushing solution to momentarily flow against blood flow toward the proximal end of the catheter. The blood flow will then carry the solution back past the distal tip of the angioscope 18, as shown in FIG. 13, to provide the bolus required for clear visualization.

The deflector 30 may be made of any smooth material, such as polyvinyl chloride or polyethylene, of sufficient rigidity to divert the flush solution in a "backward" direction. The deflector 30 should be of a diameter such that it does not extend past the outside diameter of he angioscope center catheter 10. The deflector 30 includes an opening so that angioscope 18 may be extended through the deflector 30. This allows the deflector to be bonded to the angioscope 18 just proximal to the distal tip of the angioscope 18. Of course, the deflector 30 and angioscope 18 should be bonded such that there can be no fluid flow through the interface.

In the embodiment described above, the angioscope 18 comprises a bundle of quartz fibers covered by shrink tubing. Thus, the deflector 30 is bonded to the outside of the shrink tubing. For a catheter having a diameter of 2.5 mm, the space between the respective edges of the deflector 30 and the tip of the catheter 10 is about 1–2 mm., as shown in FIG. 11.

It should be understood that the invention is not intended to be limited by the specifics of the above-described embodiment, but rather is defined by the accompanying claims.

What is claimed is:

1. An angioscope centering catheter for visualizing a vessel, the catheter comprising:
   (a) an inner catheter having distal and proximal ends;
   (b) an angioscope mounted within the inner catheter and having a distal viewing end for visualization at the distal end of the catheter;
   (c) an outer sheath having distal and proximal ends, the inner catheter being disposed within the outer sheath for sliding movement with respect to the outer sheath, the outer sheath including a plurality of longitudinal slitted sections formed circumferentially near its distal end, the outer sheath and the inner catheter being connected at their distal ends such that when the inner catheter moves proximally with respect to the outer sheath, the slitted sections splay out radially and symmetrically about the longitudinal axis of the angioscope centering catheter to center the viewing end of the angioscope within the vessel; and
   (d) a deflector shield mounted at and spaced apart from the distal end of the catheter to deflect the bolus of flushing solution provided by the catheter.

2. In an angioscope catheter apparatus of the type that includes an angioscope for visualizing the interior of a vessel, such as an artery, and an irrigating catheter that includes means for introducing flush solution to the interior of the vessel at the distal end of the angioscope, the improvement comprising a deflector shield mounted at the distal end of the angioscope such that flush solution introduced by the catheter impacts on the deflector shield.

3. An angioscope catheter apparatus for visualizing the interior of a vessel, such as an artery, the apparatus comprising:
   (a) an angioscope having a distal viewing end;
   (b) a catheter having a distal end and including means for introducing flush solution to the interior of the vessel at the viewing end of the angioscope, the angioscope being mounted within the catheter such that the viewing end of the angioscope extends beyond the distal end of the catheter; and
   (c) a curved deflector shield mounted at the viewing end of the angioscope such that flush solution introduced by the catheter is deflected by the deflector shield.

* * * * *